US011338126B1

(12) United States Patent
Mitchell et al.

(10) Patent No.: US 11,338,126 B1
(45) Date of Patent: May 24, 2022

(54) SYNCHRONOUS DRIVE SYSTEM AND METHOD OF USING SAME

(71) Applicant: The Regents of the University of Colorado, Denver, CO (US)

(72) Inventors: Max Bannister Mitchell, Castle Pines, CO (US); Jeremy N. Morgan, Missoula, MT (US)

(73) Assignee: ConneX BioMedical, Inc., Boulder, CO (US)

( * ) Notice: Subject to any disclaimer, the term of this patent is extended or adjusted under 35 U.S.C. 154(b) by 0 days.

(21) Appl. No.: 17/351,082

(22) Filed: Jun. 17, 2021

(51) Int. Cl.
| | |
|---|---|
| *A61M 60/40* | (2021.01) |
| *A61M 60/863* | (2021.01) |
| *A61B 17/34* | (2006.01) |
| *A61B 17/3207* | (2006.01) |
| *A61B 90/00* | (2016.01) |
| *A61B 17/11* | (2006.01) |
| *A61B 17/02* | (2006.01) |

(52) U.S. Cl.
CPC ... *A61M 60/863* (2021.01); *A61B 17/320708* (2013.01); *A61B 17/3468* (2013.01); *A61B 90/02* (2016.02); *A61B 2017/0243* (2013.01); *A61B 2017/1103* (2013.01)

(58) Field of Classification Search
CPC .............. A61M 60/861; A61M 60/863; A61M 60/865; A61M 60/117; A61B 17/3468; A61B 2017/0243; A61B 2017/0237; A61B 17/11; A61B 17/3423; A62M 60/40
USPC ........................................................ 623/3.15
See application file for complete search history.

(56) References Cited

U.S. PATENT DOCUMENTS

2014/0276986 A1\* 9/2014 Hoarau .................. A61B 90/30
606/144

\* cited by examiner

*Primary Examiner* — Eduardo C Robert
*Assistant Examiner* — Christina Negrellirodriguez
(74) *Attorney, Agent, or Firm* — David G. Rosenbaum; Rosenbaum IP, P.C.

(57) ABSTRACT

A synchronous drive system for simultaneously driving more than two or more rotational tissue screws and a method for simultaneously affixing a medical device to tissue employing the synchronous drive system. The synchronous drive system is particularly configured to affix an apical cuff to cardiac muscle tissue by simultaneously driving a plurality of rotational tissue screws through the apical cuff and into cardiac muscle tissue thereby affixing the apical cuff to the cardiac muscle tissue.

20 Claims, 21 Drawing Sheets

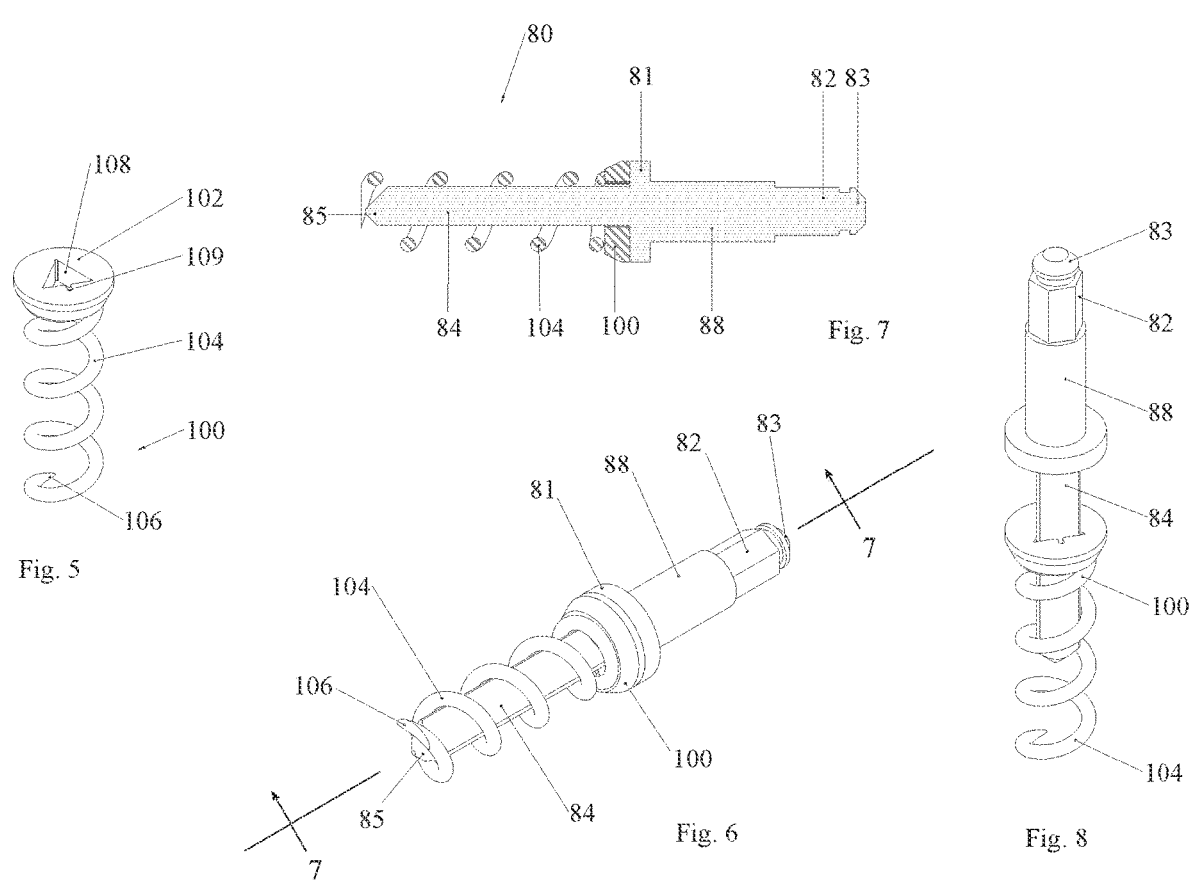

SYNCHRONOUS DRIVE SYSTEM AND METHOD OF USING SAME

BACKGROUND OF THE INVENTION

The present disclosure relates to synchronous drive systems and methods of using same to simultaneously drive two or more rotational tissue screws. More particularly, the present disclosure pertains to a synchronous drive system configured to affix an apical cuff to cardiac muscle tissue by simultaneously driving a plurality of rotational tissue screws through the apical cuff and into cardiac muscle tissue thereby affixing the apical cuff to the cardiac muscle tissue.

It is believed that synchronous drive systems configured for use in affixing an apical cuff to cardiac muscle tissue are unknown in the surgical instrumentation field.

Most current ventricular assist devices (VAD) employ a separate cardiac muscle connector component, called an apical cuff. In the usual surgical implant, the apical cuff is first attached to the left ventricular apex, a core of cardiac muscle tissue in the center opening of the apical cuff is removed to create a blood flow conduit from the left ventricle and through the apical cuff, then the pumping device is mechanically attached to the apical cuff, and the pump outlet is connected to the aorta, typically by a tubular graft. Rarely, the apical cuff and VAD pump is attached to the right atrium or right ventricle in circumstances where right ventricular or single ventricular VAD support is desired. Most conventional apical cuffs consist of a rigid metal fitting and a fabric sewing skirt coupled to the rigid metal fitting. The sewing skirt is sutured to the cardiac muscle tissue about a circumference of the fabric sewing skirt, and the pump is connected by mechanically mating it to the rigid metal fitting. The circumferential sutures provide radial compression between the cardiac muscle tissue and the fabric sewing skirt.

Conventional installation methods for apical cuffs generally involve attaching the apical cuff to the left ventricular apex with surgically placed sutures that are brought through the sewing skirt on the apical cuff. For example, a practitioner may utilize a plurality of horizontal mattress double-armed pledgeted sutures placed from the epicardial surface of the left ventricular myocardium toward the sewing skirt on the apical cuff. Each suture needle is passed through the heart and then up through the sewing skirt. After all sutures are placed, the sutures are successively tied resulting in knots on the sewing skirt. After the apical cuff is attached to the heart, a core of left ventricular muscle is removed through the center of the apical cuff, and the pump is mechanically fastened to the apical cuff. This conventional method/practice of placing pledgeted sutures is time consuming, and imperfections may result in significant bleeding complications.

A prior co-pending, commonly assigned patent application Ser. No. 17/173,914, filed Feb. 11, 2021 discloses an axial compression system employing plural tissue screws and axial compression rings or plates that bear against the sewing skirt of an apical cuff and secure the apical cuff to the cardiac muscle tissue. U.S. patent application Ser. No. 17/173,914 is hereby incorporated by reference in its entirety as teaching axial compression rings and/or axial compression plates and tissue screws, as well a method of affixing an apical cuff to cardiac muscle tissue using the same.

To solve the problem of simultaneously driving tissue screws through the sewing skirt of the apical cuff and into the heart tissue to secure the apical cuff to the heart tissue, the present disclosure provides a synchronous drive system configured to drive two or more tissue screws at the same speed and same torque, while applying little or no axial force to the tissue screws.

SUMMARY OF THE INVENTION

It is an object of the present disclosure to provide a system and method of synchronously driving two or more tissue screws into and through the sewing skirt of an apical cuff, axially securing one or more compression plates and/or rings to bear against the sewing skirt, and affix the apical cuff to heart tissue.

It is another object of the present disclosure to provide a system and method of synchronously driving two or more tissue screws at the same rate and torque to axially secure an apical cuff to heart tissue.

It is a further object of the present disclosure to provide a system and method of synchronously driving two or more tissue screws with little or no axial force applied to the tissue screws.

It is yet another object of the present disclosure to provide a system and method of targeting a desired position for affixing an apical cuff to heart tissue.

It is still another object of the present disclosure to provide a system and method for targeting a desired position for affixing an apical cuff to heart tissue, applying the apical cuff to the heart tissue at the targeted position, then affixing the apical cuff to the heart tissue by simultaneously driving two or more tissue screws through a sewing skirt to axially compress the sewing skirt against the heart tissue and affix the apical cuff to the heart tissue.

It is yet a further object of the present disclosure to provide a positioning template coupled to a synchronous drive system that both secures two or more tissue screws on the synchronous drive system and allows for pre-positioning of an apical cuff on heart tissue.

It is still another further object of the present disclosure to provide a shipping and loading tray assembly that secures the positioning template or the apical cuff to the synchronous drive system.

It is yet another object of the present disclosure to provide a synchronous drive system having a drive input sub-system, a transfer sub-system, and a driver sub-system whereby rotational input at the drive input sub-system transfers rotational force to the transfer sub-system, which, in turn, transfers rotational force to the driver sub-system and drives two or more drivers each operably coupled to a tissue screw to apply rotational force to each tissue screw simultaneously with little or no axial force applied to each tissue screw.

These and other objects, features and advantages of the disclosed synchronous drive system and its sub-systems will be more apparent to those of ordinary skill in the art from the following more detailed description of the preferred embodiments of the present disclosure taken with reference to the accompanying Figures, individually and collectively. In the accompanying Figures, like structure and/or functional features are identified by like reference numerals for ease of reference.

BRIEF DESCRIPTION OF THE DRAWINGS

FIG. 5 is a perspective view of a tissue screw employed with the synchronous drive system of the present disclosure.

FIG. 6 is a perspective view of the tissue screw engaged upon a driver component of the driver sub-system of the synchronous drive system of the present disclosure.

FIG. 7 is a cross sectional view taken along line 7-7 of FIG. 6.

FIG. 8 is another perspective view of the tissue screw engagement with the driver component of the driver sub-system of the synchronous drive system of the present disclosure.

DETAILED DESCRIPTION OF THE PREFERRED EMBODIMENTS

Figure 1:
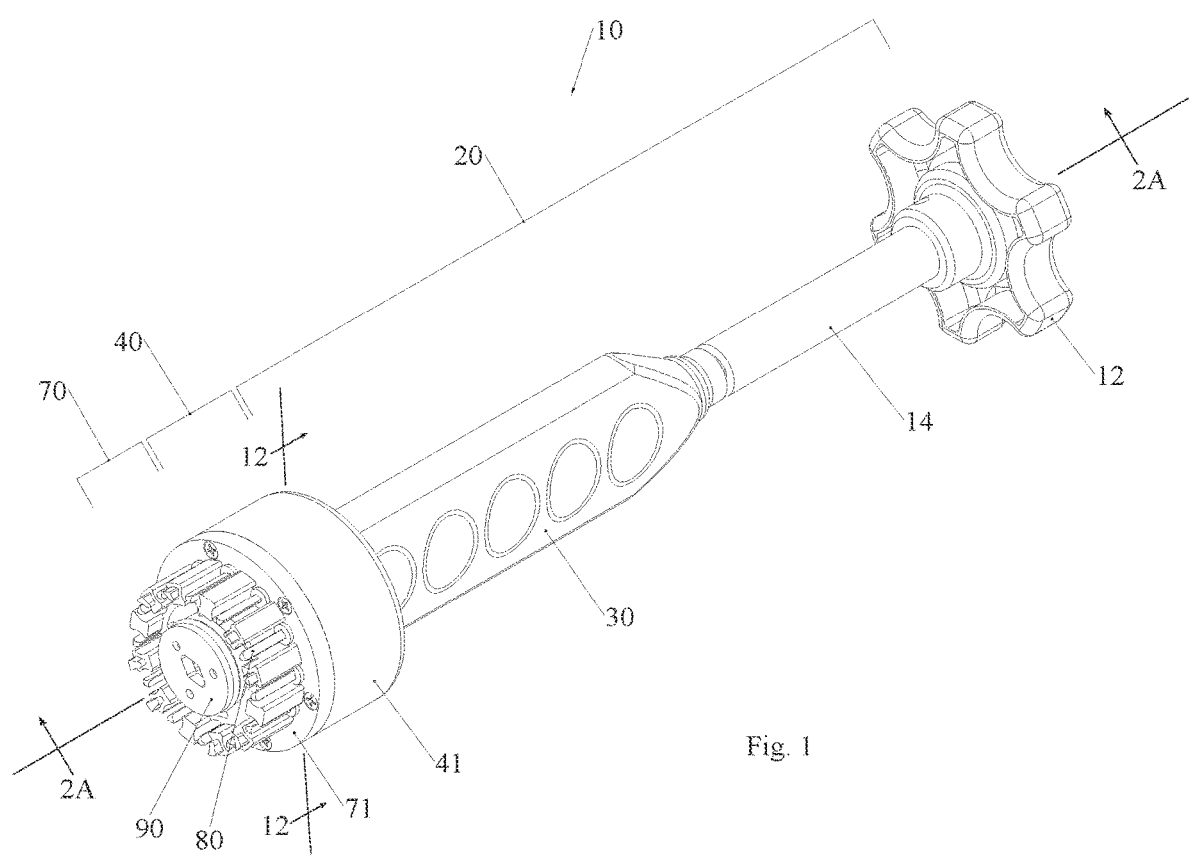
FIG. 1 is a perspective view of a synchronous drive system in accordance with the present disclosure.

The devices, system and methods of the present disclosure will be described with reference to certain exemplary embodiments thereof. These exemplary embodiments are intended to be illustrative and non-limiting examples of the present invention. The example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. Those of ordinary skill in the art will understand and appreciate that variations in materials, structure, material properties, and tolerances may be made without departing from the scope of the invention, which is defined only by the claims appended hereto and their range of equivalents. In some example embodiments, well-known processes, well-known device structures, and well-known technologies are not described in detail.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching when used throughout the figures to denote different parts but not necessarily to denote the same or different materials.

For ease of understanding, the present invention is described with reference to the accompanying Figures. In the accompanying Figures like elements are identified by like reference numerals.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"Substantially" is intended to mean a quantity, property, or value that is present to a great or significant extent and less than totally.

"About" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods, and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Figure 2A:
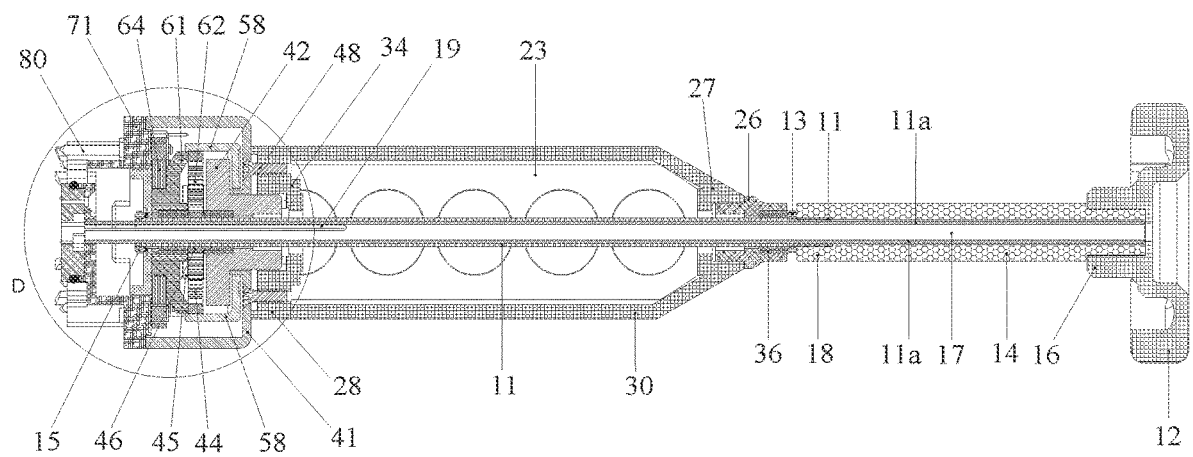
FIG. 2A is a cross-sectional view taken along line 2A-2A of FIG. 1.
Figure 2B:
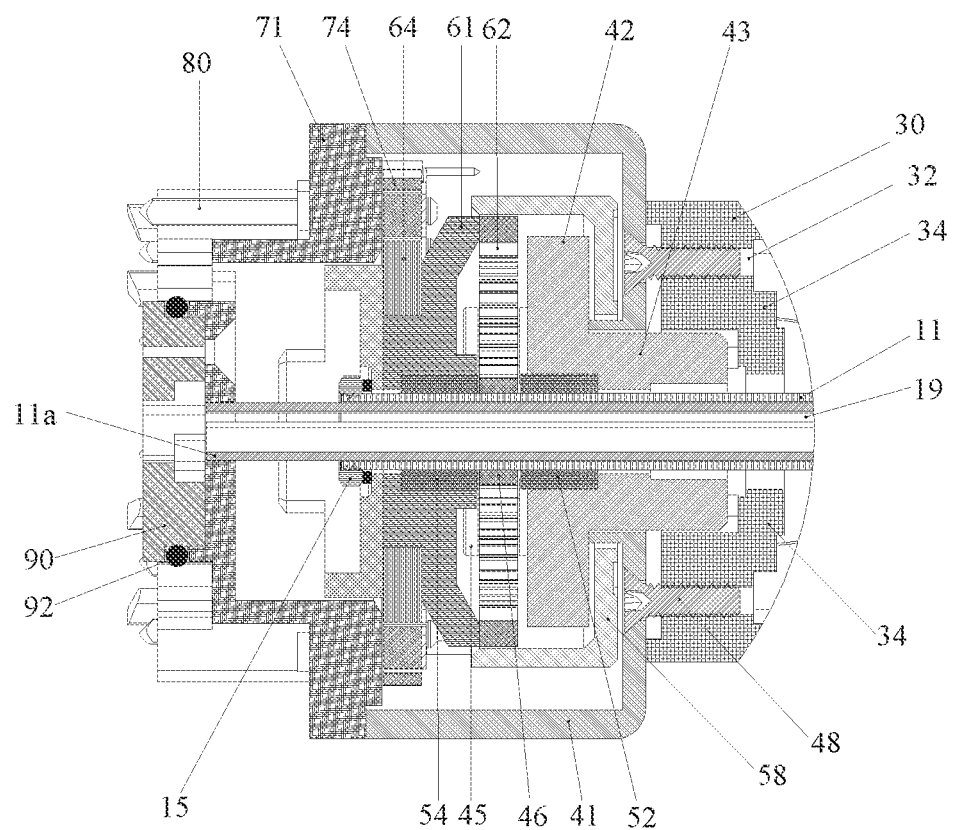
FIG. 2B is an enlarged cross-sectional view taken along section D of FIG. 2A.
Figure 3:
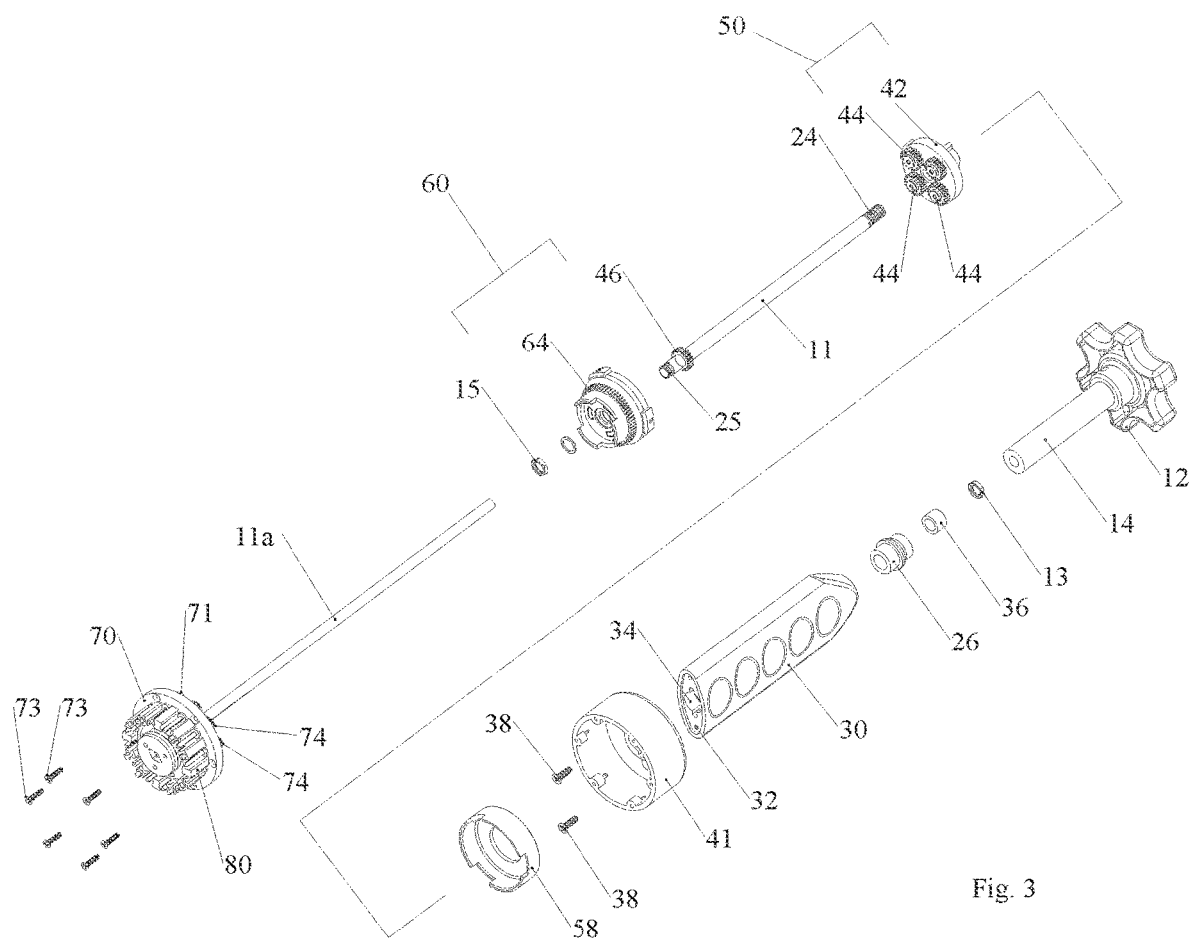
FIG. 3 is an exploded perspective view of the synchronous drive system in accordance with the present disclosure.

Turning now to FIGS. 1 through 3, inclusive of FIGS. 2A and 2B, there is shown a synchronous drive system 10 in accordance with the present disclosure. Synchronous drive system 10 includes generally a drive input sub-system 20, a drive gear sub-system 40, and a driver sub-system 70. The drive input sub-system 20 is comprised generally of a rotational input 12, such as a rotational handle, knob, or stem, that is coupled to a drive input housing 14 at coupling 16. The drive input housing 14 may be a tubular member having a drive input housing bore 17 that extends a length of the drive input housing 14 and opens at a distal end of the drive input housing 14 at a drive input housing receiver 18 having an alignment opening 19 in coaxial alignment with the drive input housing bore 17.

A driveshaft 11, which is preferably an elongate tubular member, but may, optionally, be an elongate solid member, having a proximal driveshaft end 24 and a distal driveshaft end 25, is provided and is fixedly engaged with the alignment opening 19 drive input housing receiver 18. The driveshaft 11 is positioned in coaxial alignment with the drive input housing bore 17 such that, where the driveshaft 11 is an elongate tubular member, a central lumen of the driveshaft 11 communicates with the drive input housing bore 17. Further, where the driveshaft 11 is an elongate tubular member, a center tube 11a is positioned within the central lumen of the driveshaft 11 and extends along the central longitudinal axis of the synchronous drive system 10 from the rotational input 12, within the drive input housing bore 17, through handle housing 30, drive gear sub-system 40, through driver sub-system 70, and extend to the central core 90 at the distal end of the synchronous drive system 10. The center tube 11a may have an alignment opening 19 consisting of an elongate open slot at its distal end to receive and guide a tine plate alignment projection 308 on a first shaft member 306 of an optional targeting assembly 300, as discussed in more detail below.

A handle housing 30 having proximal handle housing end 27 and a distal handle housing end 28 and an interior housing opening 23 within the handle housing 30 is provided. A handle reducing member 26 is engaged within the proximal housing end 27 and a handle housing seat 34 is positioned at the distal handle housing end 28 of the handle housing 30. Each of the proximal handle housing end 27 and the handle housing seat 34 has co-axially aligned openings that are configured to allow the driveshaft 11 to pass through each of the proximal handle housing end 27, the interior housing opening 23, and the handle housing seat 34. A bushing 36 may be engaged within the proximal housing end 27 and surrounding the driveshaft 11 seal and to allow the driveshaft 11 to rotate within the proximal housing end 27. Optionally, the rotation of driveshaft 11 may be limited by a limiting mechanism, such as a detent, stop, abutment, or the like, as are known in the art, to limit rotation of driveshaft 11. Optionally, a reducing member 26 may be provided and engaged co-axially within the proximal housing end 27 to concentrically surround the driveshaft 11. Bushing 36 may cooperate with the reducing member 26 such that both reducing member 26 and bushing 36 concentrically surround the driveshaft 11.

The handle housing seat 34 at the distal handle housing end 28 has an opening that allows the driveshaft 11 to pass therethrough. The handle housing seat 34 may have at least one securing recess 32 that is configured to receive a retaining member 48, such as a threaded screw, bolt, pin, or the like, to attach to a drive gear sub-system housing 41. It will be understood that handle housing seat 34 and drive gear sub-system housing 41 may be removably coupled to each other in a wide variety of alternative manners, such as with interference fittings, snap-fittings, tongue-and-groove fittings, or the like, instead of a securing recess 32 and a retaining member 48.

Drive gear sub-system housing 41 is an enclosure that non-rotatably couples to the handle housing 30 and houses the drive gear sub-system 40. Drive gear sub-system 40 includes a planetary gear mechanism 50 and a transfer mechanism 60 operably coupled to the planetary gear mechanism 50. Optionally, a positional indicator 58 may also be provided that is coupled to the transfer mechanism 60 and/or to the drive gear sub-system housing 41 to provide a visual and/or tactile indicia to the user of the rotational position of the transfer mechanism 60. The positional indicator 58 may also, optionally, have a positive stop to delimit the rotation of the drive gear sub-system housing 41.

Planetary gear mechanism 50 includes a planet carrier 42 having a central opening through which the driveshaft 11 passes and a planet carrier bushing 52 positioned within the central opening and concentrically surrounding the driveshaft 11. A planet carrier boss 43 may, optionally, be provided that extends proximally from the planet carrier 42 with a central opening in co-axial alignment with the central openings of the planet carrier 42, the handle housing seat 34, and the proximal handle housing end 27. Planet carrier boss 43 assists in maintaining co-axial alignment of the driveshaft 11 within the respective central openings in the planet carrier 42, the handle housing seat 34, and the proximal handle housing end 27.

An input gear 46, which acts as a sun gear, is fixedly secured to and rotatable with the driveshaft 11 at a position adjacent a distal surface of the planet carrier 42. A plurality of planet gears 44 are rotatably coupled to the distal surface of planet carrier 42 and are in operable coupling with the input gear 46, such that each planet gear 44 is rotatable about its own axis. Each of the plurality of planet gears 44 may be rotatably coupled to the planet carrier 42 by a planet gear retainer 45 that passes through a central opening in an associated planet gear 44 and into an associated one of a plurality of planet carrier retainer openings 47 in the planet carrier 42. A retaining member 48, such as, for example, a ring clip, may optionally be employed to secure the planet gear retainer 45 within each of the planet carrier retainer openings 47 and maintain each of the plurality of planet gears 44 in operable engagement with the input gear 46. Those skilled in the art will understand that a wide variety of retaining members 48 may be employed so long as they maintain the axial positioning of the planet gear retainer 45 and the associated planet gear 44 in operable engagement with the input gear 46.

Transfer mechanism 60 includes a transfer housing 61 having a ring gear 62 positioned on an inner circumference of the transfer housing 61. Transfer housing 61 has a central opening passing therethrough, and, optionally, a transfer housing bushing 54 concentrically positioned within at least a portion of the central opening of the transfer housing 61 and concentrically surrounding the driveshaft 11. The ring gear 62 is operably coupled to each of the plurality of planet gears 44. Rotation of the planet gears 44 under the influence of rotation of input gear 46 by driveshaft 11 causes the ring gear 62 and transfer housing 61 to rotate within the drive gear sub-system housing 41. A transfer gear 64 is positioned on an outer circumference of the transfer housing 61 such that rotation of the transfer housing 61 causes the transfer gear 64 to rotate.

A proximal nut 13 is engaged with a proximal end of driveshaft 11, such as by proximal threads on an outer surface of driveshaft 11, and bears against the reducing member 26, if provided, and/or bushing 36. Similarly, a distal nut 15 is engaged with a distal end of driveshaft 11, such as by distal threads on an outer surface of driveshaft 11, and bears against a distal surface of transfer housing 61. By tightening both the proximal nut 13 and the distal nut 15 against their respective bearing surfaces, the driveshaft 11 is rotatably fixed within a central axis of the respective handle housing 30, drive gear sub-system 40, and driver sub-system 70 to rotatably drive the transfer housing 61.

It will be understood by those skilled in the art that the axis of rotation of driveshaft 11 may impart either a same or different rotational axis to the transfer housing 61 depending upon the selection and configuration of the input gear 46, the plurality of planet gears 44, and the ring gear 62.

Figure 4A:
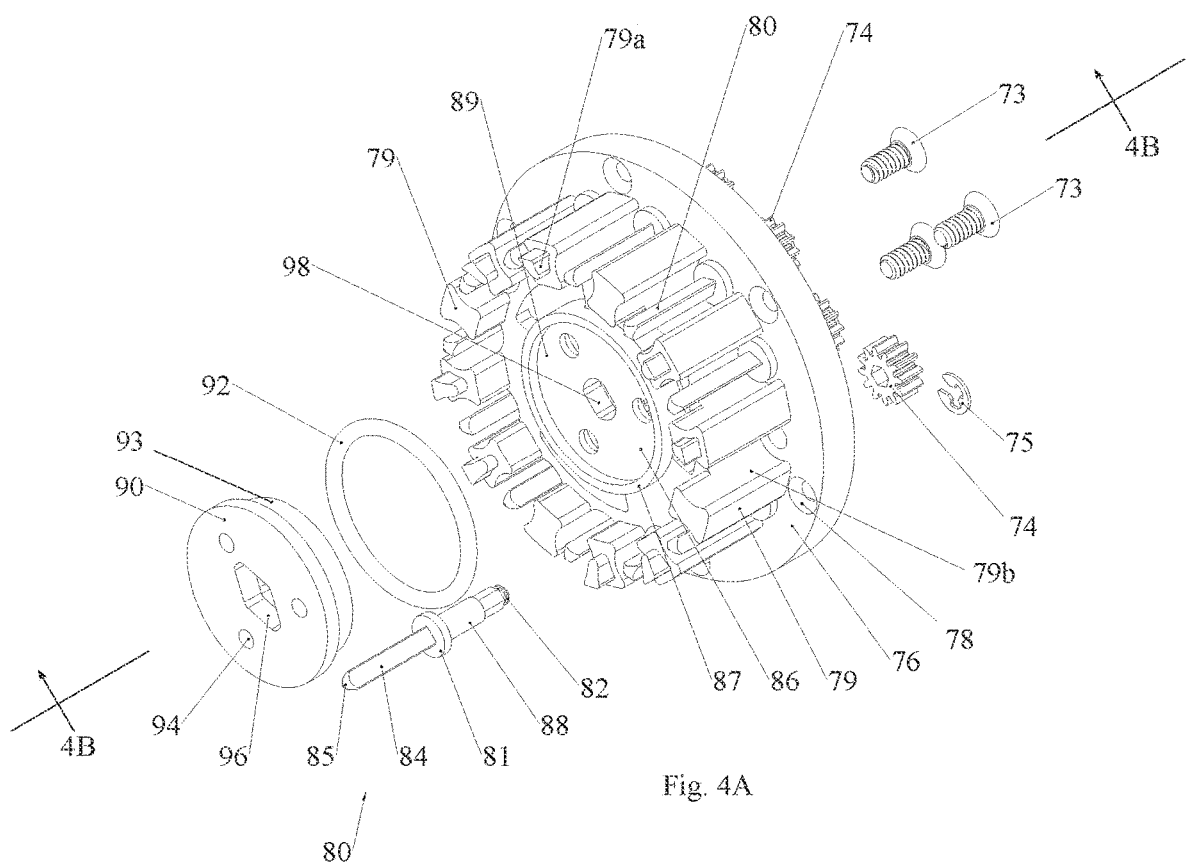
FIG. 4A is an exploded perspective view of a driver sub-system of the synchronous drive system of the present disclosure.
Figure 4B:
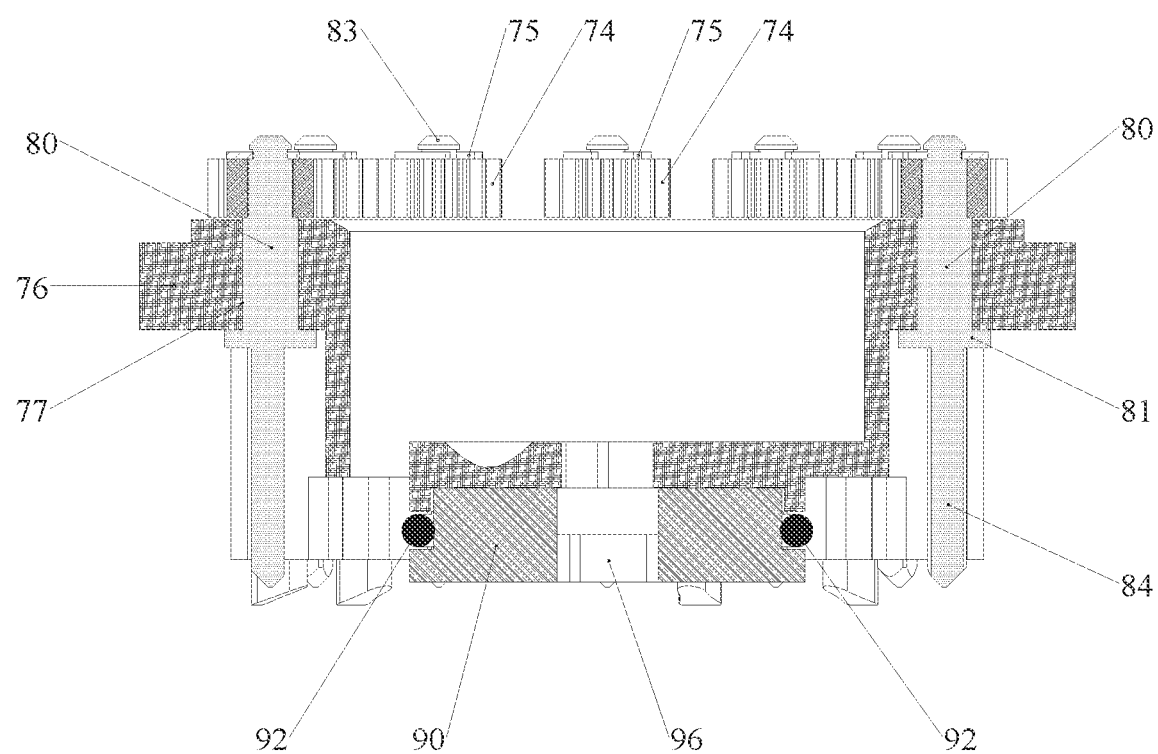
FIG. 4B is a side elevational view taken along line 4B-4B of FIG. 4A.

As illustrated in FIGS. 2B, 4A and 4B, the driver sub-system 70 is operably coupled to the transfer mechanism 60. The driver sub-system 70 includes driver carrier 71 that serves as the base for the components of the driver sub-system 70. Driver carrier 71 is configured as a generally cylindrical housing having a radially extending peripheral flange portion 76 and a driver carrier base 86. A plurality of driver openings 77 pass through the peripheral flange portion 76 and are circumferentially arrayed about the peripheral flange portion 76. The driver carrier base 86 forms a base of the driver carrier 71 and has a central opening passing through the driver carrier base 86. A plurality of tissue screw abutments 79 may, optionally, be provided and project outward from the peripheral flange portion 76 toward a distal end of the synchronous drive system 10 and a pair of tissue screw abutments 79 bound each of the plurality of driver openings 77 about the peripheral flange portion 76. Each tissue screw abutment 79 may have a curved surface 79b on two or more opposing surfaces of the tissue screw abutment 79. Curved surfaces 79b on the tissue screw abutments 79 assists in guiding tissue screws 100 as they are being engaged on each driver member 80.

A plurality of driver members 80 is provided, with each driver member 80 having a driver screw coupling 84, a driver flange 81, a collar 88, a driver gear coupling 82, and a retainer seat 83. The driver member 80 is a generally elongate member with the driver flange 81 positioned intermediate opposing ends of the driver member 80 and the driver screw coupling 84 projecting distally from the driver flange 81 and the collar 88, driver gear coupling 82, and retainer seat 83 projecting proximally from the driver flange 81, respectively. Driver screw coupling 84 preferably has a transverse cross-sectional shape configured to engage a tissue screw opening 108 in a tissue screw head 102 and pass-through tissue screw opening 108 as illustrated in FIG. 6.

The driver flange 81 is a circumferential portion of the driver member 80 that extends radially outward from the driver member 80. The collar 88 is a cylindrical element having an outer diameter greater than the driver screw coupling 84, but less than the driver flange 81. Collar 88 has a bearing surface that allows the entire driver member 80 to rotate within a respective driver opening 77 when engaged therewith. Driver gear coupling 82 extends proximally from collar 88 and has a cross-sectional shape which mates with a central opening in a drive gear 74, for example, a polygonal shape. Finally, retainer seat 83 may be a recessed circumferential groove at a proximal end of the driver member 80 and is configured to engage with a driver retainer 75, such as a removable retainer clip.

When assembled with the driver carrier 71, each driver member 80 is engaged with a corresponding driver opening 77 such that the driver screw coupling 84 is positioned between a pair of tissue screw abutments 79, with the driver flange 81 resting against a distal surface of the peripheral flange portion 76. The collar 88 is concentrically positioned at least partially within the driver opening 77 and the driver gear coupling 82 extends proximally from the driver opening 77. A drive gear 74 is engaged onto the driver gear coupling 82 and is retained on the driver gear coupling 82 by the driver retainer 75 engaged with retainer seat 83. This arrangement is consistent for each of the drivers 80 in the synchronous drive system 10.

Figure 13:
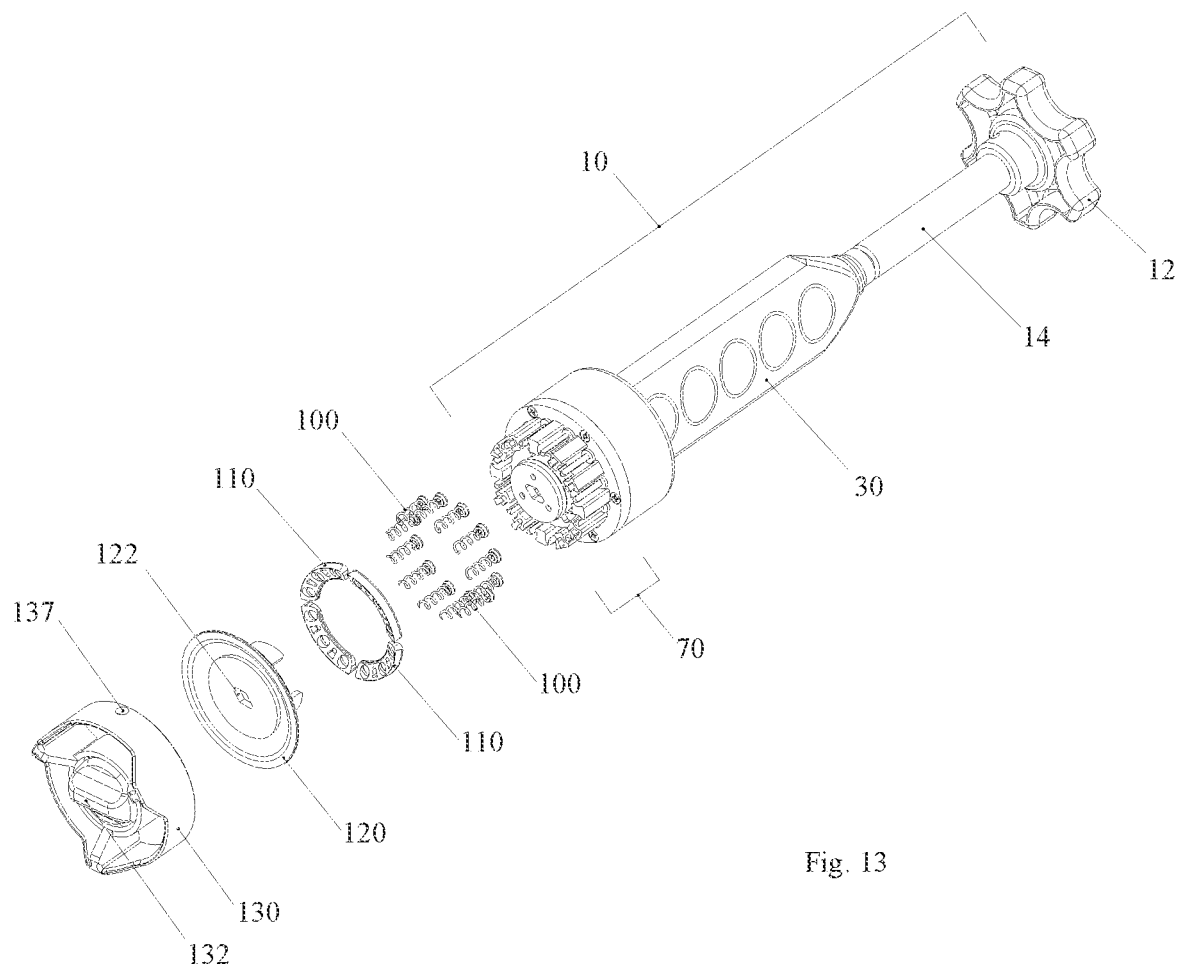
FIG. 13 is a perspective partially exploded view illustrating tissue screws, compression plates, a targeting template and a loading/shipping tray assembly or the synchronous drive system of the present disclosure.
Figure 15:
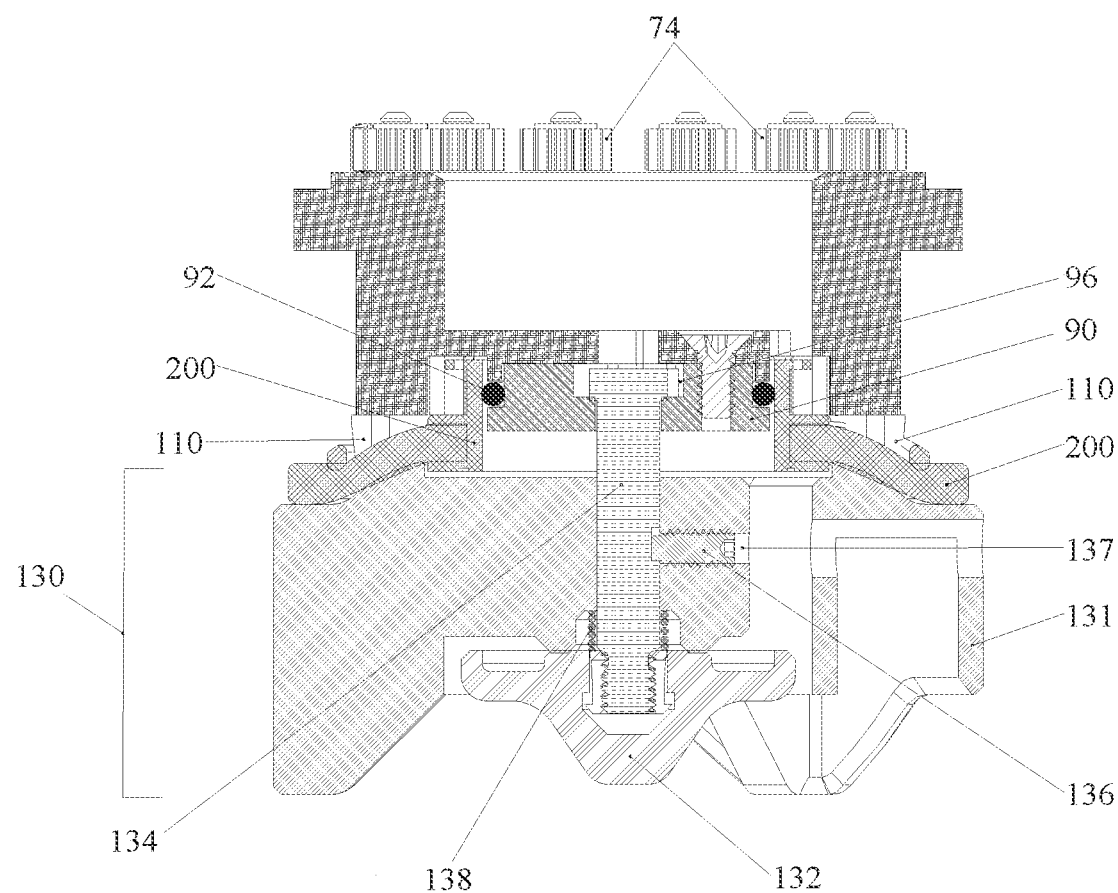
FIG. 15 is cross-sectional view taken along line 15-15 of FIG. 14.

Optionally, a central core 90 may be provided and engaged with the driver carrier base 86 on a distal aspect 89 thereof. Central core 90 is a generally cylindrical member having a boss 93 that extends proximally which is configured to mate with the distal aspect 89 of driver carrier base 86. A central core ring 92, which is a resilient member, is engaged about an outer circumference of the central core boss 93 and is compressed between the central core 90 and the distal aspect 89 of the driver carrier base 86 such that an outer circumference of the central core ring 92 protrudes beyond an outer circumference of both the driver carrier base 86 and an outer circumference of the central core 90. The central core 90 is retained in engagement with the driver carrier base 86 by at least one of a plurality of attachment members 73, such as screws, that pass through the driver carrier base 86 and engage with affixation receivers in the central core 90. The central core 90 further has a keyhole opening 96 passing centrally through the central core 90. Keyhole opening 96 is configured to accept a locking key 134 as shown in FIGS. 13 and 15.

Each of the plurality of drive gears 74 operably engage with the transfer gear 64 of transfer mechanism 60 such that rotation of the transfer mechanism 60 and the transfer gear 64 operates to rotate each of the plurality of drive gears 74 simultaneously and at the same rate to simultaneously rotate each of the drivers 80 at the same rotational rate and with the same torque. In this manner, rotational force applied to driveshaft 11 rotates the input gear 46, which, in turn, transfers rotational force to each of the planet gears 44 engaged with the ring gear 62. Resulting rotation of the ring gear 62 causes the transfer housing to rotate, thereby rotating the transfer gear 64 and driving the drive gears 74 to rotate each of the plurality of drivers 80 simultaneously. It is desirable, though optional, that a right-handed or clockwise rotation of the driveshaft 11 imparts a right-handed or clockwise rotation of each of the tissue screws 100 to cause the tissue screws 100 to rotate in a clockwise manner tradition for driving a conventional screw. To achieve this result, i.e., a clockwise rotation of the driveshaft 11 causing a clockwise rotation of the tissue screws 100, the clockwise rotation of the driveshaft 11 and the input gear 46 coupled thereto will cause a counter-clockwise rotation of the planet gears 44 engaged with the input gear 46. The counter-clockwise rotation of the planet gears 44 will, in turn, cause a counter-clockwise rotation of the ring gear 62, causing the transfer housing 61 and transfer gear 64 to both also rotate in a counter-clockwise fashion. The counter-clockwise rotation of the transfer gear 64, will then impart a clockwise rotation to the drive gears 74 and drive each of the drivers 80 in a clockwise manner as well.

According to one embodiment of the synchronous drive system 10, the gear ratio between input gear 46 and the drive gears 74 is about 5:3. This final gear ratio was selected to ensure that the transfer housing 61 made less than a 360-degree revolution about its axis and that the optional positional indicator 58 driven by the transfer housing 61, similarly, made less than a 360-degree revolution about its axis. In this manner, the positional indicator 58 will provide a visual or auditory indicia to the user of the relative rotational position of the transfer housing 61 and be capable of indicating the relative degree of rotation of the drivers 80 and the tissue screws 100.

Those skilled in the art will appreciate that if a counter-clockwise rotation of the drivers 80 is desired, the gearing of the input gear 46, planet gears 44, ring gear 62, transfer gear 64, and/or drive gears 74 may be altered such that rotational input from driveshaft 11 will cause a counter-clockwise rotation of the drivers 80 and, therefore, the tissue screws 100. Further, those skilled in the art will appreciate alternative final gear ratios, and intermediate gear ratios, i.e., between immediately engaged gears, may be selected and are within the scope of the present disclosure.

Once each of the drivers 80 are operably engaged with the driver carrier 71, tissue screws 100 may be mounted on the drivers 80. As shown in FIGS. 5-8, tissue screw 100 has tissue screw head 102 having a tissue screw opening 108 passing through a central axis of the tissue screw head 102. A clocking indicator 109 may optionally be provided on or in the tissue screw head 102 as part of the tissue screw opening 108 to provide a visual indication of the rotational position of the tissue screw 100. A helical coil 104 extends downwardly from the tissue screw head 102 and terminates in a coil tapered end 106. Coil tapered end 106 is configured to penetrate into and through the sewing skirt of an apical cuff 200 (FIG. 16) and into heart tissue 500 (FIGS. 19-22). Tissue screw opening 108 has a matching transverse profile to the transverse cross-sectional profile of driver screw coupling 84, e.g., polygonal, as illustrated tissue screw opening 108 has a triangular profile and driver screw coupling 84 has a triangular transverse cross-sectional profile. Tissue screw opening 108 is dimensioned to accommodate driver screw coupling 84 to pass therethrough with substantially no resistance to translational movement of the tissue screw 100 relative to the driver gear coupling 84 and with the ability to translate torque from the driver screw coupling 84 to the tissue screw head 102 and the helical coil 104.

When the tissue screw 100 is engaged with the driver member 80, the tissue screw head 102 is adjacent to or may be abutting a distal surface of the driver flange 81. The driver screw coupling 84 extends through the tissue screw opening 108 and passes within a central space defined by the helical coil 104. In this manner, helical coil 104 circumferentially surrounds a substantial length of the driver screw coupling 84. It will be understood that by having the driver screw coupling 84 passing through the tissue screw opening 108, torque applied to the driver screw coupling 84 will bear against the tissue screw opening 108 and transfer the rotational force from the driver screw coupling 84 to the tissue screw head 102 and cause the helical coil 104 to rotate. When the coil tapered end 106 of helical coil 104 is engaged with either the sewing skirt of an apical cuff 200 and/or with heart tissue 500, the helical coil 104 will be drawn into the sewing skirt of apical cuff 200 and/or the heart tissue 500 under the influence of the rotational force of the driver screw coupling 84 and the tissue screw head 102 will translate along a longitudinal axis of the driver screw coupling 84 until the torque applied to the tissue screw head 102 is discontinued. In this manner, substantially no axial force is applied by the driver member 80 to the tissue screw 100 and the rotational force applied by rotation of the driver member 80 to the tissue screw 100 is substantially the only force applied to the tissue screw 100.

Optionally, driver screw coupling 84 has a driver tapered end 85 that projects slightly beyond the coil tapered end 106. This slight projection of the driver tapered end 85 facilitates penetration of the coil tapered end 106 into the sewing skirt of the apical cuff by bearing onto the sewing skirt surface prior to the coil tapered end 106 engaging with the sewing skirt and assists in preventing the sewing skirt from riding up the coil as the tissue screw is being driven into and through the sewing skirt.

Figure 9:
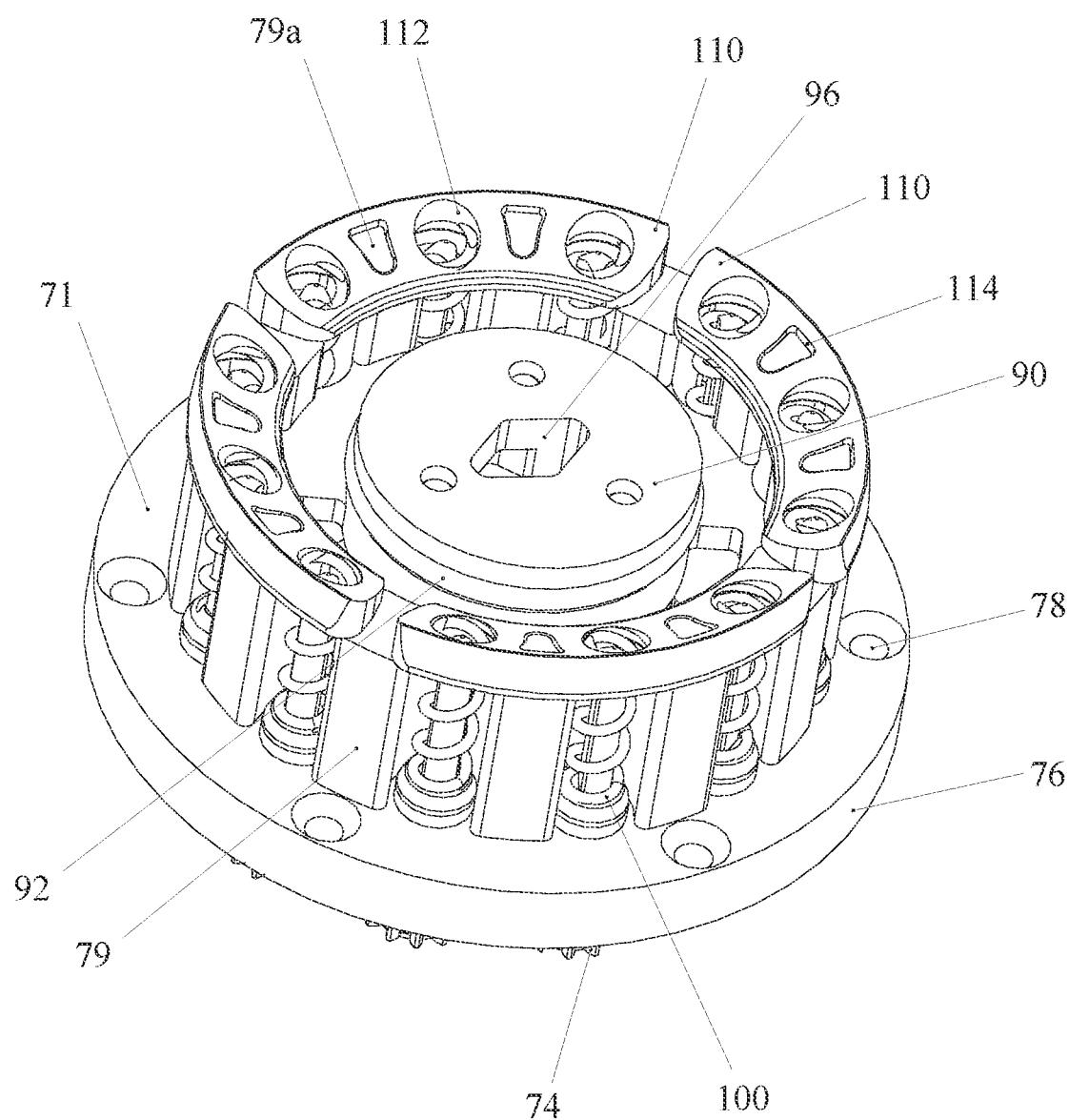
FIG. 9 is a perspective of the driver sub-system of the synchronous drive system, with tissue screws and compression plates engaged therewith.

FIG. 9 illustrates the fully assembled driver sub-system, with the tissue screws 100 engaged upon the drivers 80, the central core 90 with the central core ring 92 slightly protruding beyond the perimeter of the central core 90, the keyhole opening 96 in the central core, and the driver carrier 71 and peripheral flange portion 76, together with driver carrier affixation openings 78 that allow the driver sub-system 70 to be coupled to the drive gear sub-system housing 41. Also shown in FIG. 9 are the axial compression plates 110, which are more fully described in co-pending U.S. patent application Ser. No. 17/173,914 which is hereby incorporated by reference in its entirety. Axial compression plates 110 have a primary opening 112 that is positioned in the axial compression plate 110 in co-axial alignment with at least one corresponding driver member 80 and tissue screw 100. Axial compression plates 110 also have at least one secondary opening 114 that is in co-axial alignment with an abutment projection 79a that extends from some of the tissue screw abutments 79. The at least one secondary opening 114 has a geometry that is configured to removably mate with the geometry of the abutment projection 79a and serves to assist in mounting the axial compression plates onto the driver carrier 71 and tissue screw abutments 79 and guide axial alignment of the primary openings 112 with the drivers 80 and tissue screws 100.

Figure 10:
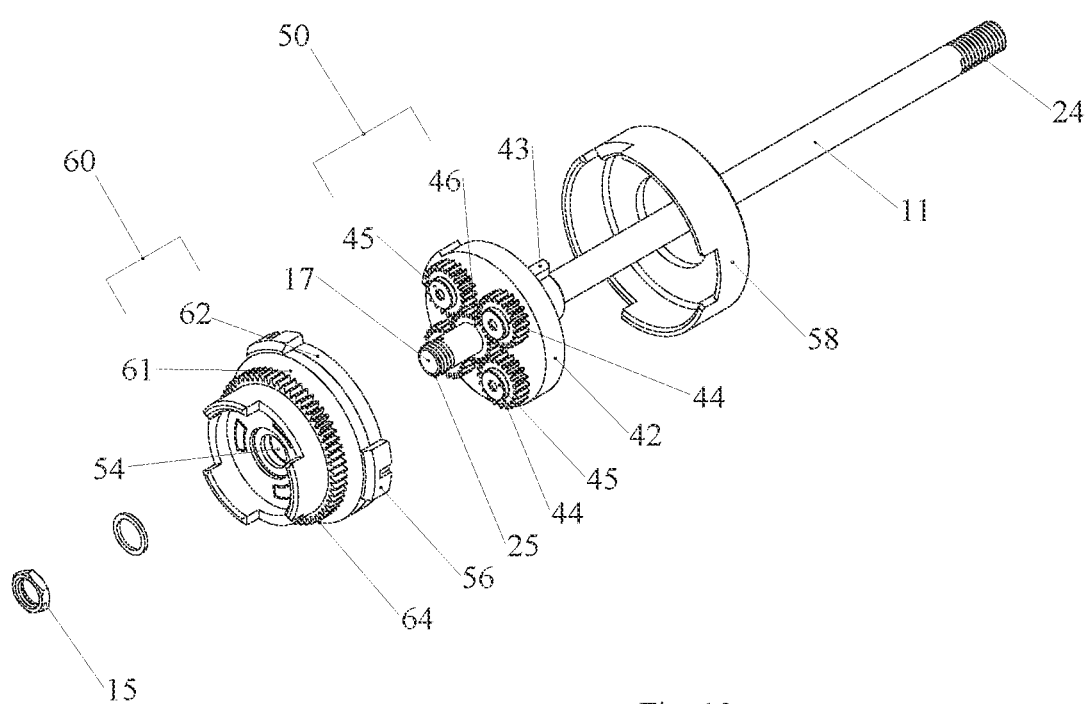
FIG. 10 is a partially exploded perspective view of a drive input sub-system and drive transfer sub-system of the synchronous drive system of the present disclosure.

FIG. 10 illustrates the axial alignment of the planetary gear mechanism 50 with the transfer mechanism 60 in driver sub-system 70. Transfer housing 61 may, optionally, be provided with one or more transfer housing projections 56 on an outer circumference of the transfer housing 61. The transfer housing projections 56 serve as alignments and abutments with the positional indicator 58 to facilitate co-rotation of the transfer housing 61 with the positional indicator 58.

Figure 11:
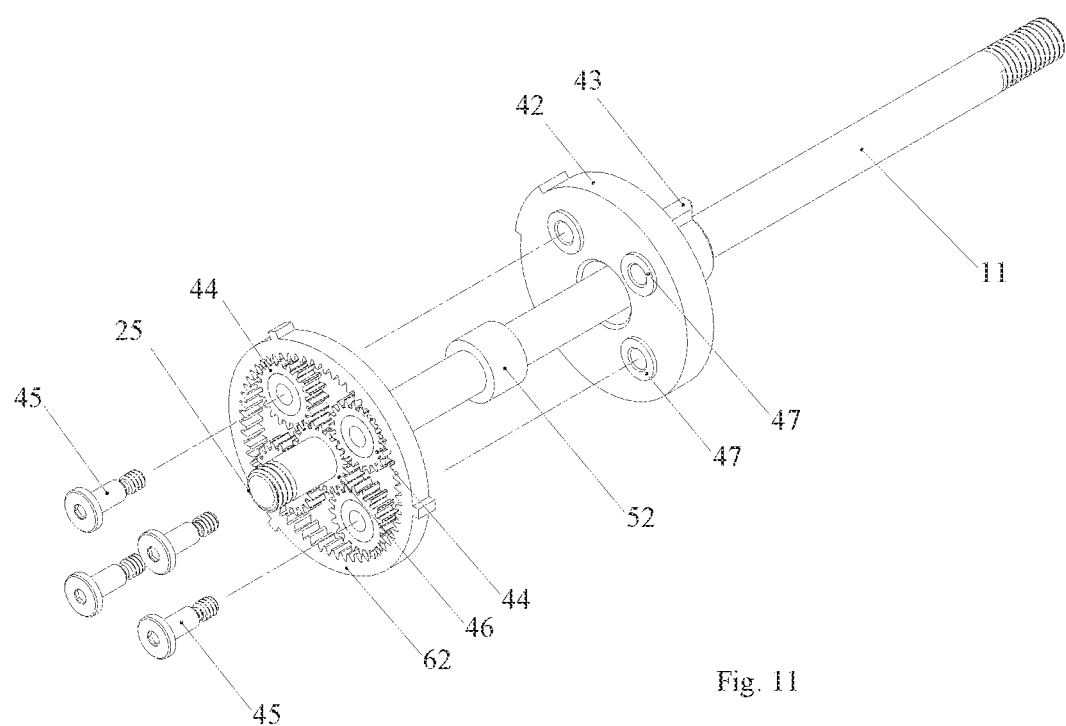
FIG. 11 is a partially exploded perspective view of the drive input sub-system of the synchronous drive system of the present disclosure.

FIG. 11 is an exploded view illustrating the engagement of the planetary gear mechanism 50 with the ring gear 62 within the transfer housing 61 (not shown) and the planet carrier 42 showing the planet carrier retainer openings 47 which receive the planet gear retainers 45 therethrough to couple the planet gears 44 to the planet carrier 42.

Figure 12:
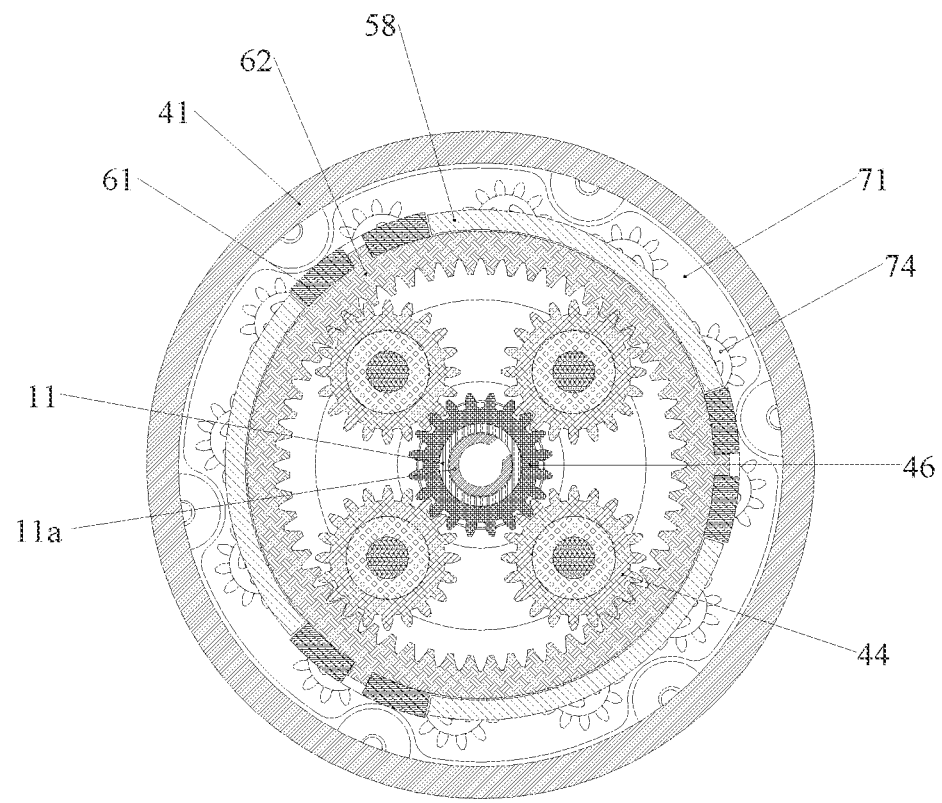
FIG. 12 is an end elevational cross-sectional view taken along line 12-12 of FIG. 1 illustrating the assembled drive input sub-system and the drive sub-system of the synchronous drive system of the present disclosure.

FIG. 12 is a cross-sectional view taken along line 12-12 of FIG. 1 and showing the driveshaft 11 with input gear 46, the surrounding planet gears 44 engaged with input gear 46, ring gear 62 in transfer housing 61 engaged with the planet gears 44, the drive gears 74 which are engaged with the transfer gear 64 (not shown), and the drive gear sub-system housing 41 enclosing the entire drive gear sub-system 40.

FIG. 13 is an exploded view showing assembly of the tissue screws 100, axial compression plates 110, an apical cuff template 120 and a loading/shipping tray 130 in their respective positions along the longitudinal axis of the synchronous drive system 10. The apical cuff template 120 is a representation of the apical cuff 200 and has an identical diameter and profile of the apical cuff 200. Apical cuff template 120 serves two functions: first, it serves to abut the axial compression plates 110 and tissue screws 100 and retain their position on the tissue screw abutments 79 and drivers 80, respectively, second, it serves as a gross positioning template for the surgeon to use on the heart tissue 500 during the VAD implantation procedure. The template keyhole 122 in the apical cuff template allows the locking key 134 in the loading/shipping tray 130 to pass through the apical cuff template and into and through the keyhole opening 96 to removably secure the loading/shipping tray 130, the apical cuff template 120, the axial compression plates 110, and the tissue screws 100 to the central core 90 and the driver sub-system 70.

Figure 14:
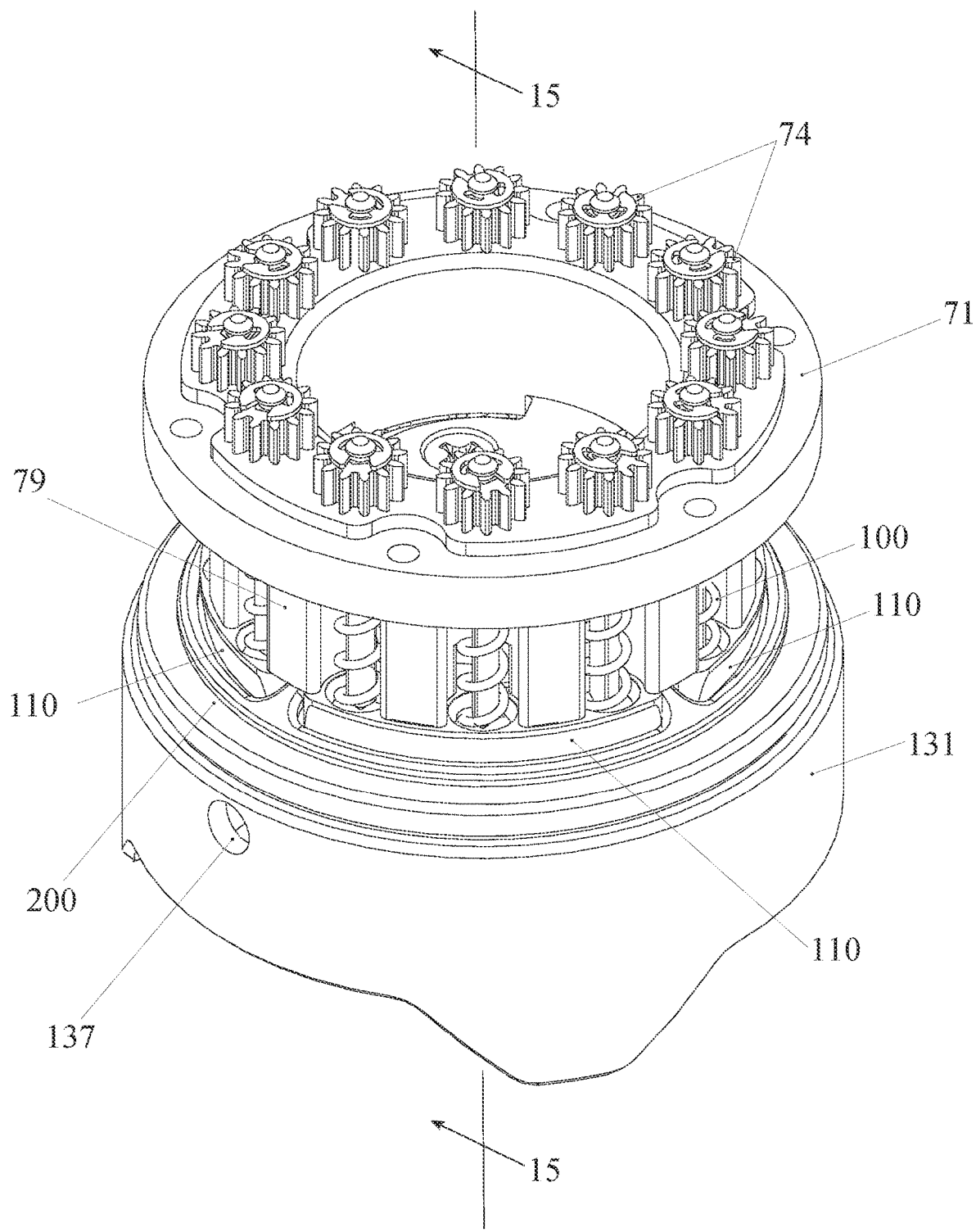
FIG. 14 is a perspective view showing engagement between the driver sub-system, compression plates, a ventricular assist device apical cuff and a loading/shipping tray assembly of the synchronous drive system of the present disclosure.

FIGS. 14 and 15 are alternative views illustrating engagement between the driver sub-system 70, tissue screws 100, axial compression plates 110, apical cuff 200, and the loading/shipping tray 130. Loading/shipping tray 130 has a tray handle 132 coupled to the locking key 134 and a tray housing 131. A spring member 138 is co-axially and concentrically engaged about the locking key 134 and bears against the tray handle 132 on one end and against the tray housing 131 on an opposing end thereof. Tray housing 131 is configured to engage with a distal surface of both the apical cuff template 120 and the apical cuff 200 when the locking key 134 is engaged with the keyhole opening 96 in the central core 90. Optionally, a set screw 136 or other positive locking mechanism, such as a detent, pin, button, or the like may be employed to bear against the locking key 134 and prevent accidental rotation and/or disengagement of the locking key 134 from the keyhole opening 96 and the central core 90. The set screw 136 or other positive locking mechanism may be accessed through an aperture 137 in the tray housing 131.

Central core ring 92, as discussed above, protrudes beyond the outer circumference of the central core 90. When either the apical cuff template 120 or the apical cuff 200 is engaged with the driver carrier 71, the central core ring 92 bears against an upper portion of the apical cuff template 120 or the apical cuff 200 to create an interference fit therebetween. This interference fit between the central core ring 92 and the apical cuff template 120 or apical cuff 200 facilitates a positive engagement that assists in retaining the apical cuff template 120 or the apical cuff 200 in a fixed position against the axial compression plates 110, tissue screws 100, drivers 80, and driver carrier 71. This positive engagement is beneficial both during attachment and detachment of the loading/shipping tray 130, targeting a position of the apical cuff template 120 or the apical cuff 200 on the heart tissue 500, and/or attaching the apical cuff 200 to the heart tissue 500.

Figure 16:
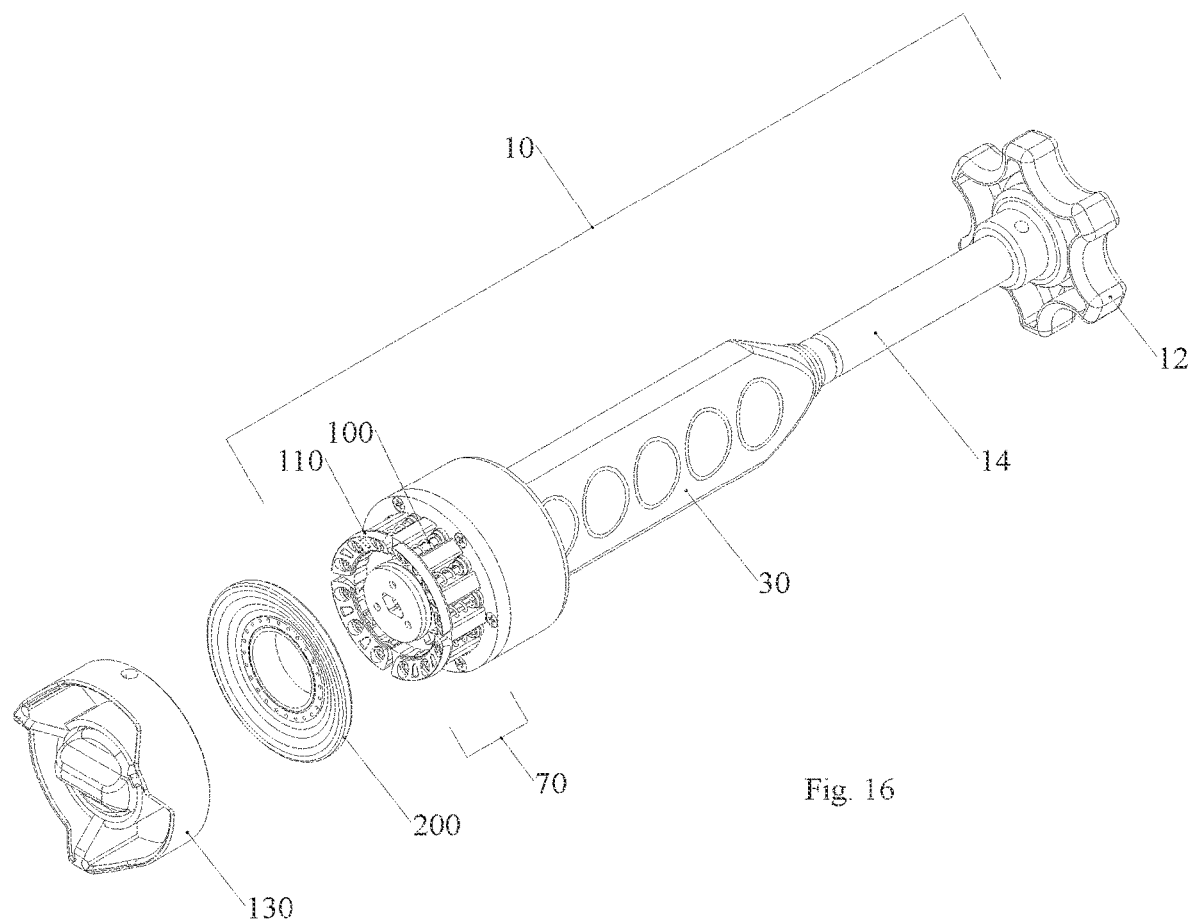
FIG. 16 is a perspective partially exploded view illustrating engagement of an apical cuff and compression plates with the synchronous drive system of the present disclosure.

FIG. 16 is an exploded view showing assembly of the tissue screws 100, axial compression plates 110, an apical cuff 200, and a loading/shipping tray 130 in their respective positions along the longitudinal axis of the synchronous drive system 10. The apical cuff 200 has a central opening through which the locking key 134 in the loading/shipping tray 130 passes to engage the keyhole opening 96 and removably secure the loading/shipping tray 130, the apical cuff 200, the axial compression plates 110, and the tissue screws 100 to the central core 90 and the driver sub-system 70.

Figure 17:
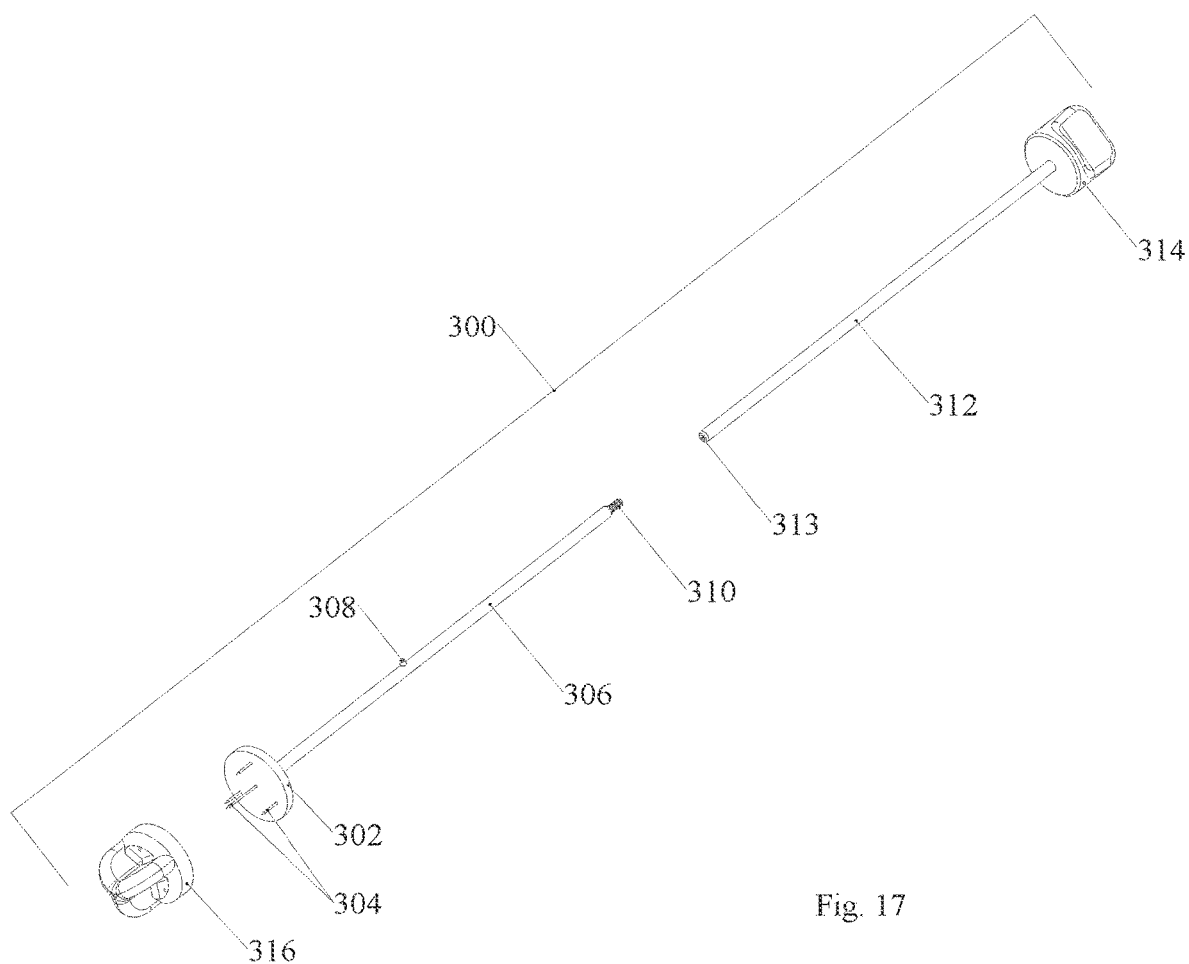
FIG. 17 is an exploded perspective view of a targeting sub-system which may, optionally, be employed with the synchronous drive system of the present disclosure.

An optional targeting assembly 300 is shown in FIG. 17. Targeting assembly 300, when employed, is co-axially and concentrically engaged and translatable within the central lumen of driveshaft 11. Targeting assembly consists of a tine plate 302 which carries one or more tines 304 arrayed about a distal surface of tine plate 302. Tines 304 are small diameter, sharpened, needle projections configured to penetrate into heart tissue 500 without significantly damaging the heart tissue 500. The tines 304 are arrayed on the distal surface of tine plate 302 in a configuration that restricts or prevents rotational movement of the tine plate 302 when the tines 304 are penetrated into heart tissue 500. A first shaft member 306 is a tine plate shaft that extends proximally from tine plate 302 and terminates in a shaft connector 310. A second shaft member 312 is a targeting handle shaft that terminates on its proximal end in a targeting handle 314 and on its distal end in a first shaft receiver 313. First shaft receiver 313 is configured to removably couple to the shaft connector 310. Shaft connector 310 may be an externally threaded male member and first shaft receiver 313 may be an internally threaded female member to accommodate threaded engagement therebetween. Targeting handle 314 may be configured as a manually manipulatable handle or configured as a connector for a robotic manipulatable handle. Finally, a tine guard 316 may be provided that engages with the tine plate 302 and the plurality of tines 304 to cover and protect both the tines 304 and the user during use of the synchronous multi-drive system 10.

Figure 18:
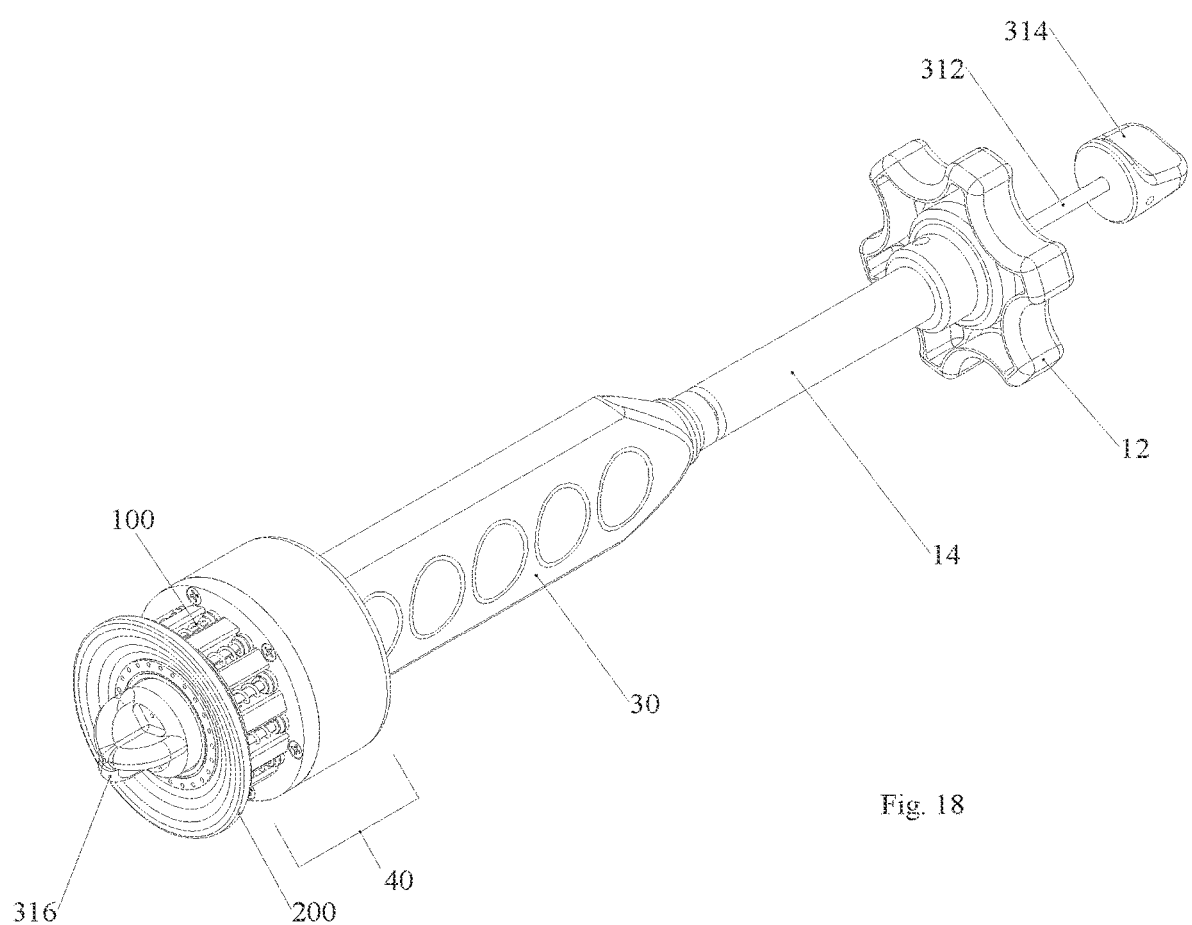
FIG. 18 is a perspective view of the assembled synchronous drive system, apical cuff and optional targeting sub-system.
Figure 19:
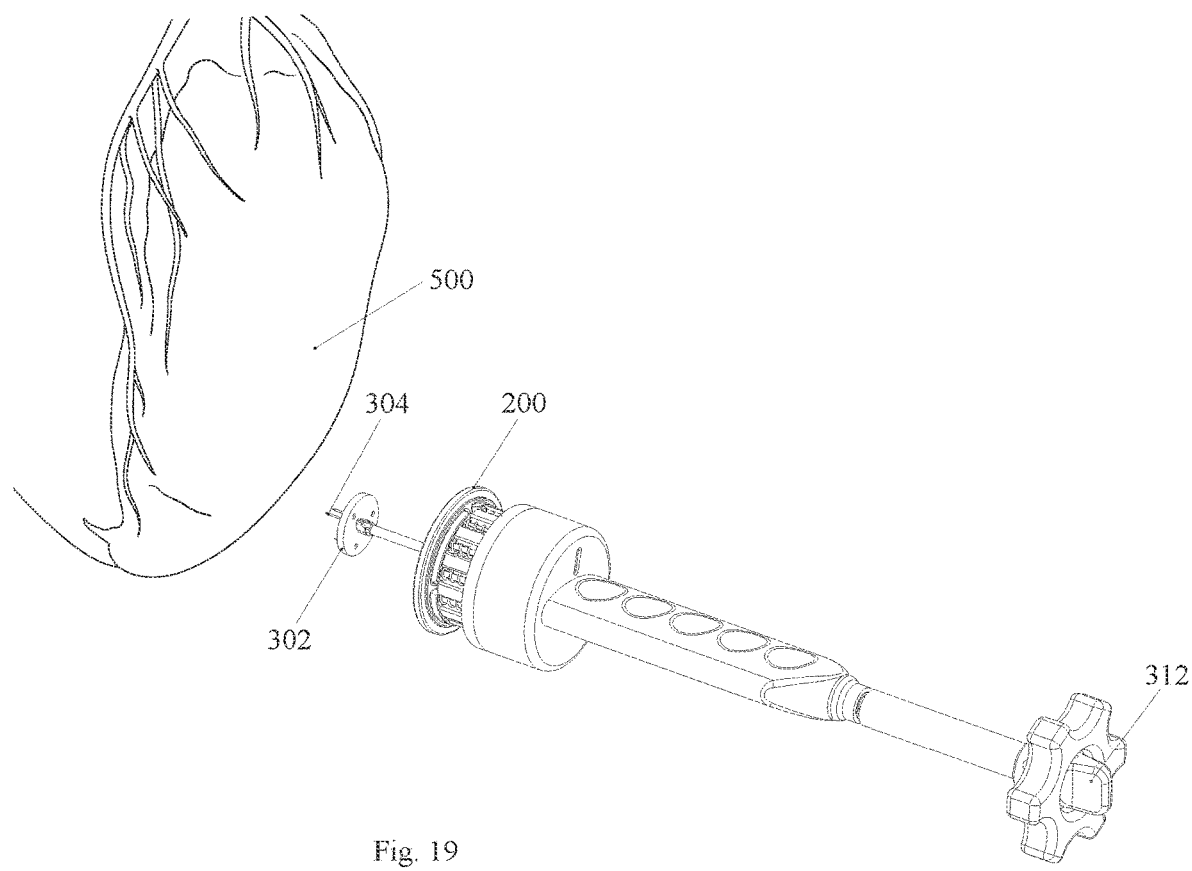
FIG. 19 is a perspective view illustrating operation of the optional targeting sub-system with the synchronous drive system showing positioning relative to a heart prior to engaging the optional targeting sub-system with the heart.
Figure 20:
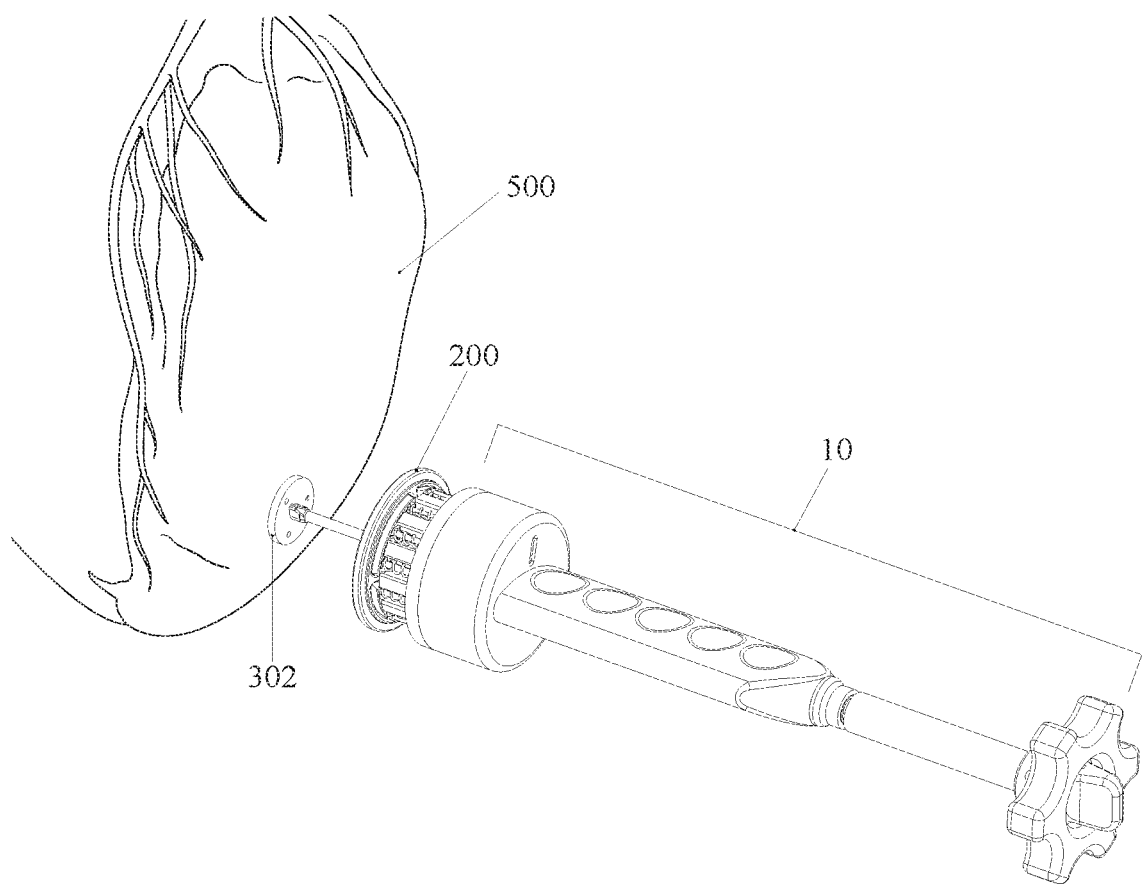
FIG. 20 is a perspective view illustrating engagement of the optional targeting sub-system with a heart.
Figure 21:
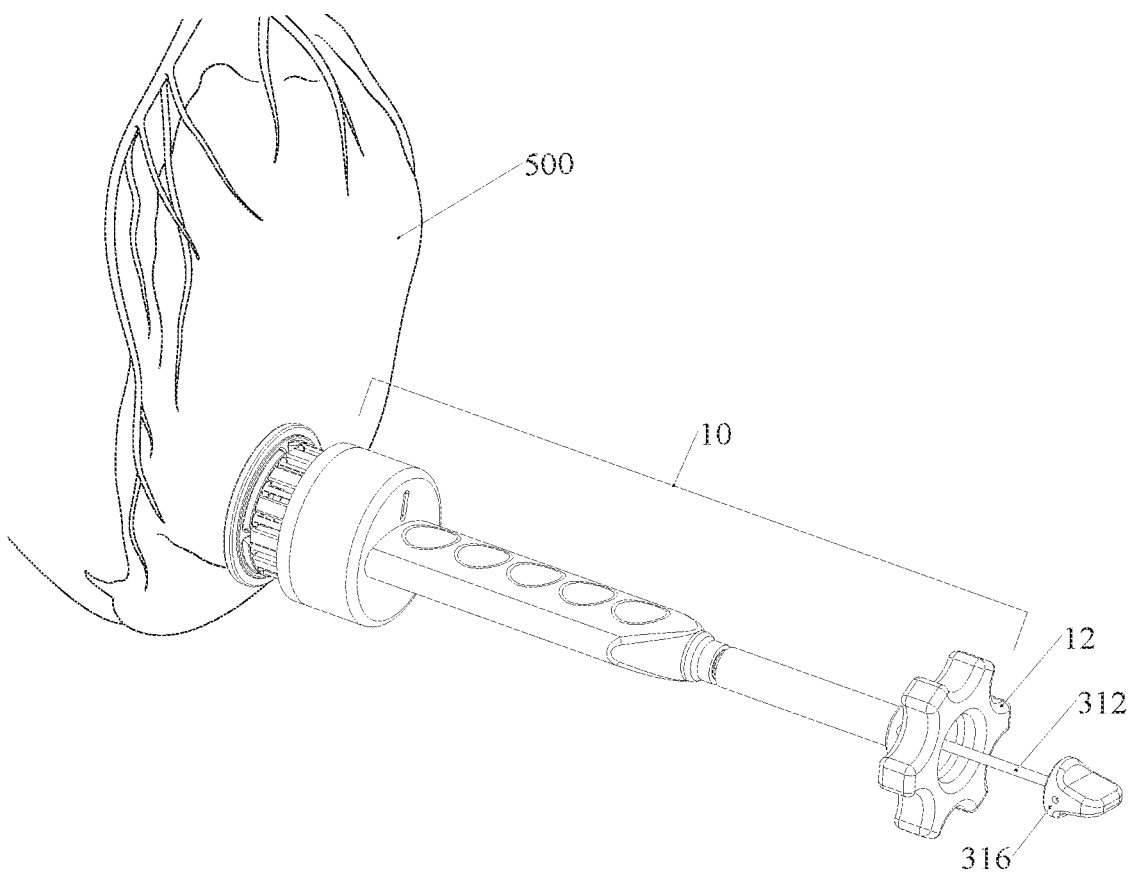
FIG. 21 is a perspective view illustrating engagement of an apical cuff and the synchronous drive of the present disclosure with a heart.
Figure 22:
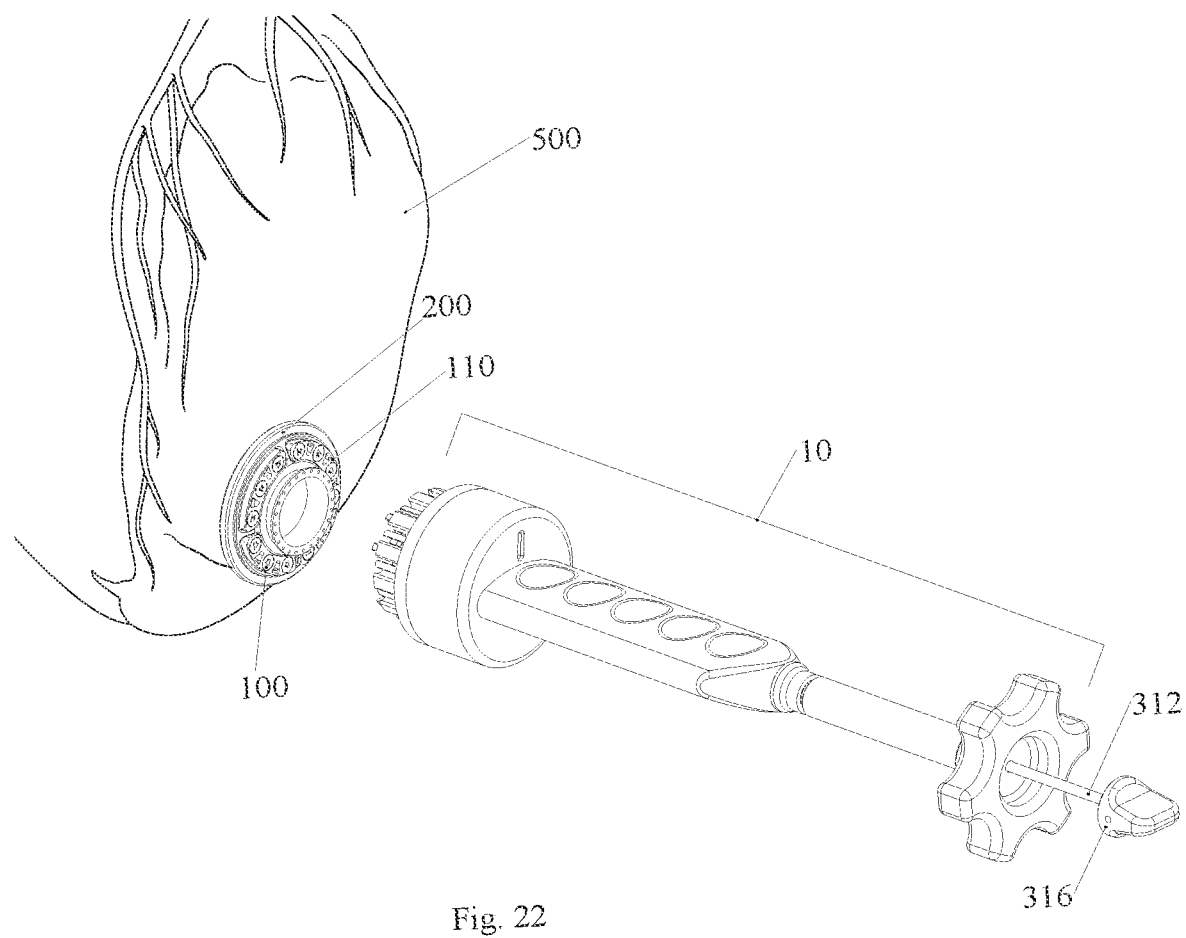
FIG. 22 is a perspective view illustrating disengagement of the synchronous drive system of the present disclosure after affixation of an apical cuff to a heart.

As illustrated in FIG. 18, first shaft member 306 carrying the tine plate 302, a plurality of tines 304 and, optionally, the tine guard 316, is engaged within a distal end of the central lumen of the driveshaft 11 by passing the proximal end of the first shaft member 306 with the shaft connector 310, through the central opening in the apical cuff, through the keyhole opening 96 in the central core 90, and into the central lumen of the driveshaft 11. The second shaft member 312 is engaged within a proximal end of the central lumen of driveshaft 11 by passing the distal end of the second shaft member 312 and the first shaft receiver 313 through a central opening in the rotational input 12, into and through the drive input housing bore 17 and into the central lumen of the driveshaft 11 until the shaft connector 310 and the first shaft receiver 313 are removably coupled.

FIGS. 19-22 illustrate the method of targeting a position on a heart tissue 500 by extending tines 304 on tine plate 302 by translating targeting handle 314, and second shaft member 312 and first shaft member 306 through the center tube 11a and driveshaft 11. Penetrating the tines 304 into the heart tissue 500 such that the tine plate 302 abuts the heart tissue. Repositioning the tines 304 and tine plate 302, may be performed if required. Then translating the synchronous drive system 10 over the first shaft member 306 and second shaft member 312 until the apical cuff 200 abuts the heart tissue 500, then rotating the rotational input 12 to simultaneously drive the tissue screws 100 into the heart tissue 500 thereby axially compressing both the axial compression plates 110 against the sewing skirt of apical cuff 200 and the apical cuff 200 against the heart tissue 500. Once the tissue screws 100 have been rotatably driven into the heart tissue 500, the synchronous drive system 10 and the targeting assembly 300 is withdrawn by disengaging the tines 304 and the tine plate 302 from the heart tissue 500, through the central opening in the apical cuff 200. At this point, the apical cuff 200 is coupled to the heart tissue 500 by tissue screws 100 and the surgeon may then adjust the torque of each of the tissue screws 100 as desired for both hemostasis and affixation. Then, the surgeon may proceed with the remainder of procedures required for VAD attachment to the apical cuff.

While the present disclosure has been made with reference to the accompanying Figures and exemplary and alternative embodiments or variants of the present invention, it will be understood that the present disclosure is not intended to be limited only to the described elements, embodiments, materials, methods, assemblies, structures, dimensions, geometries or the like. Rather, the scope of the present disclosure is intended to be restricted only by the claims appended hereto. Variations in sizes, shapes, geometries, combinations, assemblies, materials or the like are expressly contemplated by the present disclosure.

What is claimed is:

1. A synchronous multi-driver tool for affixing an apical cuff to a heart, comprising:

a. A rotatable driveshaft;
b. At least one of a plurality of first gears independently rotatable and mounted onto a planet carrier, the planet carrier being coupled to a drive input housing;
c. An input gear coupled to a driveshaft, the driveshaft being concentrically positioned within the drive input housing and operably engaged with each of the at least one of a plurality of first gears;
d. A transfer housing having a first ring gear and a second gear, the first ring gear operably coupling to the at least one of a plurality of first gears;
e. A plurality of drive gears independently rotatably mounted onto a driver carrier, the plurality of drive gears being operably coupled to the second gear of the transfer housing and the driver carrier being coupled to the drive input housing; and
f. A plurality of driver members coupled to the plurality of drive gears through a plurality of openings in the driver carrier, the plurality of driver members projecting in an opposite direction on the driver carrier from the plurality of drive gears, wherein each of the plurality of driver members is rotatable with one of the plurality of drive gears, the plurality of driver members being configured to drive a plurality of tissue screws through the apical cuff and into heart tissue.

2. The synchronous multi-driver tool of claim 1, wherein the plurality of tissue screws are removably coupled to the plurality of driver members.

3. The synchronous multi-driver tool of claim 1, further comprising a plurality of compression plates engaged with the plurality of tissue screws.

4. The synchronous multi-driver tool of claim 2, further comprising an apical cuff coupled to the plurality of tissue screws and engaged with the driver carrier.

5. The synchronous multi-driver tool of claim 3, further comprising an apical cuff coupled to the plurality of tissue screws, engaged with the plurality of compression plates and removably engaged with the driver carrier.

6. The synchronous multi-driver tool of claim 2, further comprising a positioning template removably engaged with the driver carrier and abutting an end of the plurality of tissue screws.

7. The synchronous multi-driver tool of claim 6, further comprising an end housing removably engageable with the positioning template and the driver carrier.

8. The synchronous multi-driver tool of claim 4, further comprising an end housing removably engageable with the apical cuff and the driver carrier.

9. The synchronous multi-driver tool of claim 1, further comprising a target probe having a plurality of needle projections extending from a distal end of the target probe and an elongate shaft extending proximally from the plurality of needle projections, the elongate shaft being configured to pass through and be reciprocally movable within the driveshaft.

10. The synchronous multi-driver tool of claim 9, wherein the elongate shaft further comprises a first shaft member and a second shaft member, the first shaft member extending proximally from the plurality of needle projections and the second shaft member being removably engageable with the first shaft member and having a handle at a proximal end thereof.

11. The synchronous multi-driver tool of claim 9, wherein the driveshaft further includes a center tube having an alignment opening on a distal aspect thereof, and the elongate shaft further includes an alignment projection extending a perpendicularly from the elongate shaft, wherein the alignment projection and the alignment opening on the center tube cooperate with one another.

12. The synchronous multi-driver tool of claim 1, further comprising a handle housing positioned adjacent the driver carrier and the transfer housing and circumferentially over the driveshaft such that the driveshaft is rotatable within the handle housing.

13. The synchronous multi-driver tool of claim 1, further comprising an indicia that provides a visual indication of a position of the plurality of tissue screws.

14. The synchronous multi-driver tool of claim 1, further comprising a limiter configured to limit rotation of the driveshaft.

15. The synchronous multi-driver tool of claim 1, wherein the first ring gear has a gear ratio of 1:3 with the driveshaft.

16. The synchronous multi-driver tool of claim 15, wherein the plurality of drive gears have a gear ratio with the second gear of 5:1.

17. The synchronous multi-driver tool of claim 1, wherein each of the plurality of tissue screws further comprise a tissue screw head and a helical coil extending from a surface of the tissue screw head and circumscribing an axial opening within the helical coil, the tissue screw head further having an opening passing through a central axis of the tissue screw head in axial alignment with the axial opening within the helical coil.

18. The synchronous multi-driver tool of claim 17, wherein the opening in the tissue screw head is configured to accommodate one of the plurality of driver members to pass there through and into the axial opening within the helical coil.

19. The synchronous multi-driver tool of claim 18, further comprising a clocking indicator associated with the tissue screw opening.

20. The synchronous multi-driver tool of claim 19, wherein the clocking indicator is in axial alignment with an opposing end of the helical coil.

* * * * *